United States Patent [19]

Beauchamp

[11] Patent Number: 5,043,339
[45] Date of Patent: Aug. 27, 1991

[54] ANTIVIRAL COMPOUNDS

[75] Inventor: Lilia M. Beauchamp, Raleigh, N.C.

[73] Assignee: Burroughs Wellcome Co., Research Triangle Park, N.C.

[21] Appl. No.: 452,543

[22] Filed: Dec. 18, 1989

[30] Foreign Application Priority Data

Dec. 19, 1988 [GB] United Kingdom ............. 8829571
Mar. 7, 1989 [GB] United Kingdom ............. 8905159

[51] Int. Cl.$^5$ .................. A61K 3/505; C07D 239/47
[52] U.S. Cl. ............................... 514/274; 514/261; 514/262; 544/276; 544/277; 544/317
[58] Field of Search ................... 544/317; 514/274

[56] References Cited

U.S. PATENT DOCUMENTS

| 4,548,819 | 10/1985 | De Clercq et al. | 544/277 |
| 4,567,182 | 1/1986 | Farraris | 544/277 |
| 4,868,187 | 9/1989 | Ogilvie | 544/317 |

FOREIGN PATENT DOCUMENTS

| 49072 | 4/1982 | European Pat. Off. | 544/317 |
| 77460 | 4/1983 | European Pat. Off. | 544/265 |
| 0167385 | 1/1986 | European Pat. Off. | |
| 308065 | 3/1989 | European Pat. Off. | 544/276 |
| 2104070 | 3/1983 | United Kingdom | |
| 2122618 | 1/1984 | United Kingdom | 544/276 |
| 2130204 | 5/1984 | United Kingdom | |

*Primary Examiner*—Cecilia Shen
*Attorney, Agent, or Firm*—Donald Brown; Lawrence A. Nielsen; Hannah O. Green

[57] ABSTRACT

The present invention relates to amino acid esters of pyrimidine and purine nucleosides containing an acyclic side chain, and their use in medical therapy, particularly the treatment of herpes virus infections. Also provided are pharmaceutical formulations and processes for the preparation of compounds according to the invention.

6 Claims, No Drawings

ANTIVIRAL COMPOUNDS

The present invention relates to novel antiviral esters of pyrimidine and purine nucleosides containing an acyclic side chain.

European Patent Specification No. 167385A describes and claims the antiviral pyrimidine nucleoside 1-[2-hydroxy-1-(hydroxymethyl)ethoxymethyl]cytosine and its physiologically acceptable salts and esters. The parent compound has been found to have particularly potent activity against cytomegalovirus (CMV) and Epstein-Barr virus (EBV).

The compound 9-[(2-hydroxy-1-hydroxymethylethoxy)methyl]guanine, which has the approved name ganciclovir, is described in UK Patent Specification No. 2104070A which also describes generally the pharmaceutically acceptable salts and certain esters of ganciclovir. Ganciclovir has been found to have potent activity against viruses of the herpes family particularly herpes simplex and cytomegalovirus. Ganciclovir has however, low oral bioavailability and is typically administered as a 1-hour intravenous infusion every 12 hours.

The 6-deoxy and 6-amino analogues of ganciclovir have also been described in the literature, the former being described in UK Patent Specification No. 2104070A and the latter in UK Patent Specification No. 2130204A.

We have now found that amino acid esters of the compounds referred to above surprisingly have advantageous bioavailability when administered by the oral route, resulting in exceptionally high levels of the parent compound in the body. This enables less drug to be administered while still providing equivalent drug levels of the parent compound in the plasma. Oral administration means patient compliance is considerably simplified.

According to one feature of the present invention there is provided a compound of formula I:

(wherein R and $R^1$ are independently selected from a hydrogen atom and an amino acid acyl residue providing at least one of R and $R^1$ represents an amino acid acyl residue and B represents a group of formula

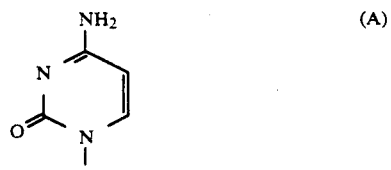

or

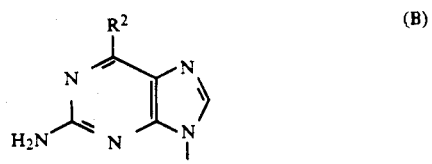

in which $R^2$ represents a $C_{1-6}$ straight chain, $C_{3-6}$ branched chain or $C_{3-6}$ cyclic alkoxy group, or a hydroxy or amino group or a hydrogen atom) and the physiologically acceptable salts thereof.

A group falling within formula (I) above is where $R^2$ represents a hydroxy or amino group or a hydrogen atom.

It will be appreciated that the compound of formula (I) in which B represents a group of formula (B) wherein $R^2$ represents hydroxy is shown in the enol tautomeric form. The compound may also exist in its keto tautomeric form.

Among the above amino acid esters of formula (I) those of cytosine and ganciclovir are particularly preferred by virtue of their especially improved bioavailability in comparison with the parent compounds.

The amino acid acyl residue of the above compounds according to the invention may be derived for example from naturally ocurring amino acids, preferably neutral amino acids i.e. amino acids with one amino group and one carboxyl group. Examples of preferred amino acids include aliphatic acids, e.g., containing up to 6 carbon atoms such as glycine, alanine, valine and isoleucine. The amino acid esters according to the invention includes the mono- and di-esters of the compound of formula (I). The amino acids may be D-, L- and DL-amino acids, with the L-amino acids being most preferred.

Examples of preferred compounds of formula (I) above include those of Examples 1 to 6.

The above-mentioned physiologically acceptable salts are preferably acid addition salts derived from an appropriate acid, e.g., hydrochloric, sulphuric, phosphoric, maleic, fumaric, citric, tartaric, lactic or acetic acid.

The above-defined amino acid esters of formula (I) and their salts which are hereinafter referred to as the compounds according to the invention, are especially useful for the treatment of virus infections, especially herpes infections such as herpes simplex, varicella zoster, Epstein-Barr virus (human herpes virus-6 infections), and particularly cytomegalovirus, in humans or non-human animals. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and -retinitis, particularly in immunocompromised patients including renal and bone marrow transplant patients and patients with Acquired Immune Deficiency Syndrome (AIDS). Epstein-Barr virus (EBV) causes infectious mononucleosis, and is also suggested as the causative agent of nasopharyngeal cancer, immunoblastic lymphoma, Burkitt's lymphoma and hairy leukoplakia.

According to further features of the present invention we provide:

(a) the compounds according to the invention for use in medical therapy particularly for the treatment of viral infections, e.g., those referred to above;

(b) the use of the compounds according to the invention for the manufacture of a medicament for the treatment of viral infections, e.g., those referred to above;

(c) a method for the treatment of a herpes viral infection, especially a cytomegalovirus infection, in a subject which comprises administering to the subject an effective amount of a compound according to the invention.

The compounds according to the invention may be administered for therapy by any route appropriate to the condition to be treated, suitable routes including oral, rectal, nasal, topical (including buccal and sublingual), vaginal and parenteral (including subcutaneous, intramuscular, intravenous, intradermal, intrathecal, intraocular and epidural). It will be appreciated that the preferred route may vary with for example the condition of the recipient.

For each of the above-indicated utilities and indications the amount required of the compound according to the invention will depend upon a number of factors including the severity of the condition to be treated and the identity of the recipient and will ultimately be at the discretion of the attendant physician. In general however, for each of these utilities and indications, a suitable, effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of the compound according to the invention per unit dosage form.

The compounds of the invention may be administered for the treatment of viral infections alone or in combination with other therapeutic agents, for example, with other antiviral agents such as 9-(2-hydroxy-ethoxymethyl)guanine (acyclovir) used to treat herpes viral infections in particular HSV; with 3'-deoxy-3'-azidothymidine (zidovudine) or a 2',3'-dideoxynucleoside for example 2',3'-dideoxycytidine, 2',3'-dideoxyinosine, 2',3'-dideoxyadenosine or 2',3'-dideoxyguanosine, used to treat retroviral infections in particular Human Immunodeficiency Virus (HIV) infections, interferons particularly α-interferon and soluble proteins such as CD4, or any other agents such as analagesics or antipyretics which when in combination with a compound of the invention provide a beneficial therapeutic effect.

While it is possible for the active ingredients to be administered alone it is preferable to present them as pharmaceutical formulations. The formulations, both for veterinary and for human use, of the present invention comprise at least one compound according to the invention (also referred to hereafter as "the active ingredient"), together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutanous, intramuscular, intravenous, intradermal, intrathecal, intraocular and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e., by rapid inhalation through the nasal passage from a container of powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule, drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispersing agent are included. These formulations preferably contain from 15 to 85% of the active ingredient.

The compounds according to the invention may be prepared in conventional manner, e.g. by a process as described below.

Thus, according to a further feature of the present invention we provide a process for the preparation of the compounds according to the invention which comprises reacting the compound of formula (II)

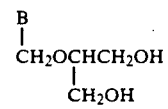

(wherein B is as hereinbefore defined) with an optionally protected amino acid or functional equivalent thereof and optionally effecting one or more of the following conversions:

(i) removal of any protecting groups;
(ii) where the resulting product is a compound of formula (I), conversion of the said compound into a physiologically acceptable salt thereof; and
(iii) where the resulting product is a physiologically acceptable salt of a compound of formula (I), conversion of the said salt into the parent compound.

In the above process, the reaction may be carried out in a conventional manner, for example in a solvent such as pyridine, dimethylformamide etc., in the presence of a coupling agent such as N,N'-dicyclohexylcarbodiimide, optionally in the presence of a catalytic base such as 4-dimethylaminopyridine. The water formed during the reaction may, if desired, be removed in conventional manner, for example by distillation or by the addition of a water-binding substance. Subsequently, the ester obtained as reaction product may be isolated in conventional manner.

As an alternative to the use of the amino acid per se, a functional equivalent of the acid may be employed, e.g., an acid halide such as the acid chloride, or an acid anhydride.

In order to avoid undesirable side-reactions, it may be advantageous to use an amino-protected derivative, examples of preferred amino-protecting groups including acyl, e.g., $C_{1-4}$alkanoyl such as acetyl; arylalkyloxycarbonyl, e.g., benzyloxycarbonyl; or amino-precursor groups such as azido groups. It is particularly preferred to employ an amino acid protected by a benzyloxycarbonyl group. Such benzyloxycarbonyl protected compounds are commercially available, e.g., from Sigma Chemical Co., U.S.A., or may be prepared by treating the appropriate amino acid with carbobenzoxy chloride in alkaline solution.

The optional conversions (i), (ii) and (iii) may be effected in a conventional manner. Thus, for example, removal of protecting groups in conversion (i) may be effected by hydrogenolysis or as appropriate. With regard to removal of protecting groups on the amino acid acyl radicals, hydrogenolysis, e.g., of arylalkyloxycarbonyl protecting groups, and conversion of azido group, e.g., by catalytic hydrogenation, e.g., using a palladium catalyst, are preferred.

The conversion of an amino acid ester into a physiologically acceptable salt may be effected in conventional manner, e.g., by treatment of the compound with an appropriate acid to form an acid addition salt.

Similarly, conversion of a salt into the parent amino acid ester may be effected in conventional manner for example, by treatment with a stoichiometric amount of an ion exchange resin (basic form), filtration to remove the resin and lyophilisation of the resulting solution.

The following Examples illustrate the present invention.

EXAMPLE 1

(a) 2-((4-(N-((Benzyloxy)carbonyl)-L-isoleucinamido)-1,2-dihydro-2-oxo-1-pyrimidinyl)methoxy)-1,3-propanediyl bis(N-((benzyloxy)carbonyl)-L-isoleucinate) and 2-((4-Amino-1,2-dihydro-2-oxo-1-pyrimidinyl)methoxy)-1,3-propanediyl bis(N-((benzyloxy)carbonyl)-L-isoleucinate)

A suspension of 2 g of 4-amino-1-((2-hydroxy-1-(hydroxymethyl)ethoxy)methyl)-2(1H)-pyrimidinone in 40 mL dry dimethylformamide (DMF) was warmed to 60° C. to give a colorless solution. 7.4 g of CBz-L-isoleucine, 567 mg of dimethylaminopyridine (DMAP) and 5.75 g of dicyclohexylcarbodiimide (DCC) were successively added. A white precipitate was observed after 15 min. The mixture was allowed to stir at room temperature for 4 days. The resulting suspension was filtered and the filtrate was dried (MgSO4), filtered and evaporated in vacuo to a light yellow oil. The oil was purified by flash chromatography on silica gel, eluting with 4:1 EtOAC-Hex to afford the triacylated derivative, 783 mg (9%), as a white foam. Elution with 5:1 EtOAc-MeOH afforded the diacylated derivative, 2.93 g (44%) as a white foam.

(b) 2-((4-Amino-1,2-dihydro-2-oxo-1-pyrimidinyl)methoxy)-1,3-propanediyl bis(L-isoleucinate)

To a cool mixture of 2.54 g of 2-((4-amino-1,2-dihydro-2-oxo-1-pyrimidinyl)methoxy)-1,3-propanediyl bis(N-((benzyloxy)carbonyl)-L-isoleucinate) and 5.16 g of 10% palladium catalyst in acetic acid was slowly added 6.4 mL of 1,4-cyclohexadiene. The mixture was allowed to stir at room temperature for 3 h. The reaction mixture was filtered through a pad of Celite, the filtrate was then concentrated and dried in the lyophiliser for 3 d. The residue was scraped off, affording 2.079 g (82%, as the acetic acid salt) of a beige foam. The elemental analysis (showing 2M of acetic acid and 1M of water), UV, $^1$H, $^{13}$C-NMR spectra were consistent with the title structure.

EXAMPLE 2

(a) 2-((4-(N-((benzyloxy)carbonyl)-L-valinamido)-1,2-dihydro-2-oxo-1-pyrimidinyl)methoxy)-1,3-propanediyl bis(N-((benzyloxy)carbonyl)-L-valinate) and 2-((4-amino-1,2-dihydro-2-oxo-1-pyrimidinyl)methoxy)-1,3-propanediyl bis(N-((benzyloxy)carbonyl)-L-valinate)

A suspension of 2 g of 4-amino-1-((2-hydroxy-1-(hydroxymethyl)ethoxy)methyl)-2(1H)-pyrimidinone in 40 mL dry dimethylformamide (DMF) was slightly warmed until a clear solution remained. 5.84 g of CBz-L-valine, 567 mg of dimethylaminopyridine (DMAP) and 4.79 g of dicylohexylcarbodiimide (DCC) was successively added. A white precipitate was observed after 15 min. The mixture was stirred at room temperature for 4 h. The resulting suspension was filtered and the filtrate distributed between water and CH2Cl2. The organic fraction was dried (MgSO4), filtered and evaporated in vacuo to a yellow oil. The oil was purified by flash chromatography of silica gel. Eluting with 2% methanol in dichloromethane afforded the triacylated derivative, 1.12 g (13%) as a white foam. Eluting with 4% methanol in dichloromethane afforded the N,O-diacylated derivative, 113 mg (2%). Eluting with 10% methanol in dichloromethane afforded the O,O-diacylated derivative, 3.44 g (54%) as a white foam.

(b) 2-((4-amino-1,2-dihydro-2-oxo-1-pyrimidinyl)methoxy)-1,3-propanediyl bis(L-valinate)

To a cool mixture of 3.44 g of 2-((4-amino-1,2-dihydro-2-oxo-1-pyrimidinyl)methoxy)-1,3-propanediyl bis(N-((benzyloxy)carbonyl)-L-valinate) and 7 g of 10% palladium catalyst in acetic acid was slowly added 8.65 mL of 1,4-cyclohexadiene. The mixture was allowed to stir at room temperature for 18 h. The reaction mixture was filtered through a pad of Celite. The filtrate was then concentrated and dried in the lyophilizer for 48 h. The resulting beige foam was scraped off affording 2.38 g (68%, as the acetic acid salt) of the title compound. The elemental analysis (showing 2M of acetic acid and 1M of water) UV, $^1$H, $^{13}$C-NMR spectra were consistent with the title structure.

EXAMPLE 3

2-((2-Amino-1,6-dihydro-6-oxo-9H-purin-9-yl)methoxy)-1,3-propanediyl bis(L-isoleucinate)

(a) 2-((2-Amino-1,6-dihydro-6-oxo-9H-purin-9-yl)methoxy)-1,3-propanediyl bis(N-((benzyloxy)carbonyl)-L-isoleucinate)

1,3-Dicyclohexylcarbodiimide (6.2 g, 0.03 mol, Aldrich) was added to a stirring suspension of N-benzyloxycarbonyl-L-isoleucine (7.96 g, 0.03 mol, Sigma), 9-((2-hydroxy-1-hydroxymethylethoxy)methyl) guanine (2.55 g, 0.01 mol), and 4-dimethylaminopyridine (0.4 g, 0.003 mol, Aldrich) in N,N-dimethylformamide (150 ml). The mixture was stirred at room temperature for four days then collected by filtration and washed with dimethylformamide (20 ml). The filtrate, including wash, was evaporated under vacuum to a slurry. A solution of this residue in dichloromethane (100 ml) was filtered, treated with silica gel (50 g, E.Merk, 230–400 mesh), and concentrated under vacuum. The residue was added to a silica gel column and subjected to flash chromatography with gradient elution starting with 100% dichloromethane and gradually increasing to 7% methanol. The product-containing fractions were concentrated under vacuum, dissolved in dichloromethane (50 ml) and washed with water (5×100 ml) to remove residual dimethylformamide. The organic layer was dried over magnesium sulphate, filtered, and evaporated under vacuum to give 4.3 g (57%) of a white solid. M.p.=60° C.(dec.); TLC(silica gel, CH2Cl2:MeOH/9:1)$R_f$=0.63; H-NMR(DMSO-d6)10.57(br s,1H), 7.78(s,1H), 7.63(d,d,2H), 7.33(m,10H), 6.41(br s,2H), 5.41(s,2H), 5.01(s,4H)m 3.87-4.23(m,7H), 1.68(m,2H), 1.20(m,4H), 0.755(m,12H): HPLC(Versapack C-18; 70% MeOH-(aq.)/0.1% TFA)k'=1.76; MS(Cl)m/z 750 (100%, M+H); UV max (MeOH)258.8 nm (22,300). Anal. Calcd. for $C_{37}H_{47}N_7O_{10}$: C,59.27; H,6.32; N,13.08. Found: C,59.18; H,6.38; N,13.02.

(b) 2-((2-Amino-1,6-dihydro-6-oxo-9H-purin-9-yl)methoxy)-1,3-propanediyl bis(L-isoleucinate)

A solution of the product of stage (a) (2.0 g, 2.66 mmol) and 10% palladium on carbon (250 mg, Aldrich) in glacial acetic acid (250 ml) was shaken on a Parr Hydrogenator under 30 to 35 psi H2 for 5 hours. Reaction progress was monitored by TLC (silica gel, CH2Cl2:MeOH/9:1). The catalyst was removed by filtration (Millipore Prefilter). Dilution of the filtrate with ether caused the product to separate as an oil. After 14 hours at 5° C., the supernatant was decanted from a colourless gum, which was dried under high vacuum to a white foam. The foam was dissolved in water (20 ml), filtered, and freeze-dried to a white foam; yield, 1.3 g (79%). H-NMR (DMSO-d6) 7.79(3,1H), 6.49(br s,2H), 5.41(s,2H), 3.9–4.2(m,4H), 3.10(d,1H), 3.06(d,1H), 1.9 (HOAc), 1.5(m,1H), 1.34(m,4H), 1.1(m,4H); 0.73–0.78(m,12H); $^{13}$C-NMR (DMSO-d$_6$) 156.80, 153.96, 151.30, 137.47, 116.30, 73.41, 70.78, 62.88, 62.57, 58.15, 24.18, 21.28, 15.33, 15.28, 11.33; HPLC (Versapack C-18; 30% MeOH (aq.)/0.1% TFA) 1 peak, k'=1.22; UV max (H$_2$O) 251 nm (12,000). MS (positive ion/Cl) m/z 482. Anal. Calcd. for C$_{21}$H$_{35}$N$_7$O$_6$.2HOAc:1H$_2$O: C,48.46; H,7.32; N,15.82. Found: C,48.52; H,7.3; N,15.75.

EXAMPLE 4

2-((2-Amino-1,6-dihydro-6-oxo-9H-purin-9-yl)methoxy)-1,3-propanediyl bis(2-aminoacetate)

(a) 2-((2-Amino-1,6-dihydro-6-oxo-9H-purin-9-yl)methoxy)-1,3-propanediyl bis(N-((benxyloxy)carbonyl)-glycinate)

9-((2-Hydroxy-1-hydroxymethylethoxy)methyl)guanine (2.55 g, 0.01 mol), N-benzyloxycarbonyl-glycine (6.28 g, 0.03 mol, Aldrich), and 1,3-dicyclohexylcarbodiimide (6.2 g, 0.03 mol, Aldrich) were added to N,N-dimethylformamide (100 ml) and stirred at room temperature for two days. The white precipitate was collected by filtration and washed with dimethylformamide (50 ml). The filtrate, including wash, was evaporated under vacuum to a slurry. A solution of the residue in dichloromethane (100 ml) was filtered and washed with brine solution (3×125 ml). The organic layer was dried over magnesium sulphate, filtered and evaporated under vacuum to a solid. A solution of the solid in dichloromethane (20 ml) was purified on a silica gel column (E.Merk, 230–400 mesh) by flash chromatography and gradient elution, starting with 100% dichloromethane and increasing by 2% increments to 8% methanol. The product fractions were evaporated to dryness under vacuum to give 5.20 g (80%) of a white powder. M.P.-120° C. (dec.): TLC (silica gel, CH$_2$Cl$_2$:MeOH/9:1) R$_f$=0.38; H-NMR(DMSO-d$_6$)10.60(s,1H). 7.80(s,1H), 7.65(t,2H), 7.32(m,10H), 6.46(br s,2H), 5.40(s,2H). 5.02(s,4H), 4.05(m,5H), 3.68(d,4H); HPLC Versapack C-18; 70% MeOH (aq.)/0.1% TFA)k'-0.89; UV max (MeOH) 254.4 nm (16.100). Anal. Calcd. for C$_{29}$H$_{31}$N$_7$O$_{10}$.0.5H$_2$O: C,53.87; H,4.99; N,15.16. Found: C,53.99; H,5.02; N,15.13.

(b) 2-((2-Amino-1,6-dihydro-6-oxo-9H-purin-9-yl)methoxy)-1,3-propanediyl bis(2-aminoacetate)

A solution of the product of stage (a) (2.0 g, 3 mmol) and 10% palladium on carbon (250 mg, Aldrich) in glacial acetic acid (250 ml) was shaken on a Parr Hydrogenator under 30 to 35 psi H$_2$ for 7 hours 19 minutes, monitored by TLC on silica gel using 10% methanol in methylene chloride. The catalyst was removed by filtration (Millipore Prefilter), the filtrate concentrated to 10 ml by vacuum, and then freeze-dried. The solid was dissolved in water, filtered, and freeze-dried again to give 1.94 g (100%) of a white solid. H-NMR (DMSO-d$_6$) 7.79(t,1H), 6.62(br s,2H). 5.40(s,2H), 4.02(m,4–5H), 3.19(s,4H) $^{13}$C-NMR (DMSO-d$_6$) 169.40. 166.04, 156.83, 153.97, 153.88, 151.31, 151.22, 137.51, 116.28, 79.92, 76.52, 73.40, 71.39, 71.20, 71.07, 63.77, 63.02, 60.76, 60.18, 44.25, 42.31, 42.18; HPLC (Versapack C-18; 20% MeOH (aq.)/0.1% TFA) 2 peaks, k'=0.06, 0.18; UV max (H$_2$O) 252 nm (12,000), 263.6 nm (8,790). Anal. Calcd. for C$_{13}$H$_{19}$N$_7$O$_6$. 4HOAc:0.5H$_2$O: C,40.78; H,5.87; N,15.85. Found: C,40.99; H,5.93; N,15.70.

EXAMPLE 5

2-((2-Amino-1,6-dihydro-6-oxo-9H-purin-9-yl)methoxy)-1,3-propanediyl bis(L-valinate)

(a) 2-((2-Amino-1,6-dihydro-6-oxo-9H-purin-9-yl)methoxy)-1,3-propanediyl bis(N-((benzyloxy)carbonyl)-L-valinate)

A solution of 22.5 g (0.09M) of N-benzyloxycarbonyl chloride (Sigma Chemical Co.) L. valine, 18.6 g (0.09 mol) of N,N-dicyclohexylcarbodiimide and 1.2 g (0.01 mol) of 4-dimethylaminopyridine in 100 mL of dimethylformamide was stirred under nitrogen for 10 minutes. After the addition of 20 mL more of dimethylformamide and 7.65 g (0.03 mol) of 9-(1,3-dihydroxypropoxymethyl)guanine, the mixture was stirred for 18 hours at ambient temperature.

The suspension was filtered, washing the precipitate with dichloromethane and the combined filtrate and washings were evaporated in vacuo. The residual yellow oil was dissolved in methanol and absorbed on silica gel. The mixture was evaporated in vacuo and the powdery residue added to a column prepared for flash chromatography. The column was eluted first with 2% methanol in dichloromethane to remove an impurity and the desired product was then eluted off with 5% methanol in dichloromethane. Evaporation of this eluate gave 14.3 g (66%) of 2-((2-amino-1,6-dihydro-6-oxo-9H-purin-9-yl)methoxy)-1,3-propanediyl bis(N-((benzyloxy)carbonyl)-L-valinate), which gave a satisfactory elemental analysis, $^1$H HMR and $^{13}$C spectra.

(b) 2-((2-Amino-1,6-dihydro-6-oxo-9H-purin-9-yl)methoxy)-1,3-propanediyl bis(L-valinate)

A mixture of 0.722 g (1.0 mmol) of 2-((2-amino-1,6-dihydro-6-oxo-9H-purin-9-yl)methoxy)-1,3-propanediyl bis(N-((benzyloxy)carbonyl)-L-valinate) and 300 mg of 10% palladium on carbon in 10 mL of acetic acid was shaken in a Parr apparatus at ambient temperature at an initial pressure of 50 psi for 18 hours. The mixture was filtered through a pad of celite, washing the pad with acetic acid. The filtrate was evaporated at room temperature under pump vacuum giving a syrup (822 mg) which was dried at 100° C. with 1.0 mm pressure. The resulting glass turned to a solid on scraping with a spatula and was the desired 2-((2-amino-1,6-dihydro-6-oxo-9H-purin-9-yl)methoxy)-1,3-propanediyl bis(L-valinate). The compound gave satisfactory $^1$H NMR, $^{13}$C, UV and Mass spectra. It analyzed for 2 moles of acetic acid and 0.05 moles of water.

EXAMPLE 6

2-((2-Amino-1,6-dihydro-6-oxo-9H-purin-9-yl)methoxy)-1,3-propanediyl bis(L-alaninate)

(a) 2-((2-Amino-1,6-dihydro-6-oxo-9H-purin-9-yl)methoxy-1,3-propanediyl bis(N-((benzyloxy)carbonyl)-L-alaninate)

A mixture of 13.4 g (0.06 mol) N-benzyloxycarbonyl-L-alanine (Sigma chemical company), 12.4 g (0.06 mol) of N,N-dicyclohexylcarbodiimide, 0.8 g (0.006 mole) of 4-dimethylaminopyridine and 5.1 g (0.02 mol) of 9-(1,3-dihydroxypropoxymethyl)guanine in 640 mL of dimethylformamide was stirred under nitrogen 18 hours at ambient temperature.

The suspension was filtered, washing the precipitate with dichloromethane and the combined filtrate and washings were evaporated in vacuo. The residual yellow oil was dissolved in methanol and absorbed on silica gel. The mixture was evaporated in vacuo and the powdery residue added to a column prepared for flash chromatography. The column was eluted first with 1:1 ethyl acetate and ether, then with acetone, to remove impurities. The desired product was then eluted off with 5% and 10% methanol in dichloromethane. Evaporation of these eluates gave 7.649 g (57%) of 2-((2-amino-1,6-dihydro-6-oxo-9H-purin-9-yl)methoxy)-1,3-propanediyl bis(N-((benzyloxy)carbonyl)-L-alaninate), which gave satisfactory $^1$H NMR and $^{13}$C spectra.

(b) 2-((2-Amino-1,6-dihydro-6-oxo-9H-purin-9-yl)methoxy)-1,3-propanediyl bis(L-alaninate)

A mixture of 1.0 g (1.5 mmol) of 2-((2-amino-1,6-dihydro-6-oxo-9H-purin-9-yl)methoxy)-1,3-propanediyl bis(N-((benxyloxy)carbonyl)-L-alaninate) and 500 mg of 10% palladium on carbon in 10 mL of acetic acid was shaken in Parr apparatus at ambient temperature at an initial pressure of 42 psi for 18 hours. The mixture was filtered through a pad of celite, washing the pad with acetic acid. The filtrate was lyophilized giving the desired 2-((2-amino-1,6-dihydro-6-oxo-9H-purin-9-yl)methoxy)-1,3-propanediyl bis(L-alaninate) as a syrup (0.98 g). Analysis by $^1$H NMR, $^{13}$C NMR, HPLC(C-18 reverse phase in 15% of 0.1% trifluoroacetic acid-acetonitrile/0.1% trifluoroacetic acid-water) and Mass spectra proved that the compound was a mixture of the O-monoesterified and O,O-diesterified in the ratio of 1:9.

The following Examples, 7 to 9, illustrate pharmaceutical formulations according to the invention where the active ingredient is a compound according to the invention.

| Example 7 | Tablet |
|---|---|
| Active compound | 200 mg |
| Lactose | 235 mg |
| Starch | 50 mg |
| Polyvinylpyrrolidone | 50 mg |
| Magnesium stearate | 5 mg |

Mix the active compound with the lactose and starch and wet granulate with a solution of the polyvinylpyrrolidone. Dry, sift, blend the granules with magnesium stearate and compress.

| Example 8 | Capsule |
|---|---|
| Active Compound | 200 mg |
| Lactose | 184 mg |
| Sodium starch glycollate | 8 mg |
| Polyvinylpyrrolidone | 6 mg |
| Magnesium stearate | 2 mg |

Mix the active compound with the lactose and sodium starch glycollate and wet granulate with a solution of the polyvinylpyrrolidone. Dry, sift, blend the granules with the magnesium stearate and fill into hard gelatin capsules.

| Example 9 | Intravenous Injections |
|---|---|
| (A) | |
| Active compound | 200 mg |
| Sodium hydroxide solution | q.s. to pH 7.0 to 7.5 |
| Example 9 | Intravenous Injections |
| Water for injections | to 5.0 ml |

Dissolve the active compound in part of the water for injections. Adjust the pH with the sodium hydroxide solution and make up to volume with additional water for injections. Under aseptic conditions, sterilise the solution by filtration, fill into sterile ampoules and seal the ampoules.

| (B) | |
|---|---|
| Active compound | 100 mg |
| Sodium hydroxide solution | q.s. to pH 7.0 to 7.5 |
| Mannitol | 125 mg |
| Water for injections | to 2.5 ml |

Dissolve the active compound and mannitol in part of the water for injections. Adjust the pH with the sodium hydroxide solution and make up to volume with additional water for injections. Under aseptic conditions, sterilise the solution by filtration, fill into sterile vials and remove the water by freeze-drying. Seal the vials under an atmosphere of nitrogen and close with a sterile stopper and aluminium collar.

What is claimed is:

1. A compound of formula (I):

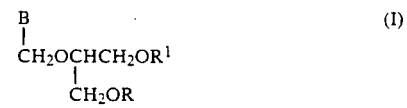

wherein R and $R^1$ are independently selected from a hydrogen atom and a naturally occurring neutral amino acid acyl residue providing at least one of R and $R^1$ represents a naturally occurring neutral amino acid acyl residue and B represents a group of formula

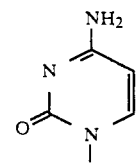

or a physiologically acceptable salt thereof.

2. A method of treatment of herpes viral infection in a subject which comprises administering to the subject an effective antiviral amount of compound of formula (I) as defined in claim 1 or a physiologically acceptable salt thereof.

3. A method according to claim 2 for the treatment of cytomegalovirus infections.

4. A pharmaceutical formulation comprising as active ingredient a compound of formula (I) as claimed in claim 1 or a physiologically acceptable salt thereof together with at least one pharmaceutically acceptable carrier therefor.

5. A pharmaceutical formulation as claimed in claim 4 adapted for oral or parenteral administration.

6. A pharmaceutical formulation as claimed in claim 4 in the form of a tablet or capsule.

* * * * *